United States Patent [19]

Hanssen

[11] Patent Number: 4,688,563

[45] Date of Patent: Aug. 25, 1987

[54] SURGICAL DRAPE AND ARRANGEMENT FOR SECURING THE SURGICAL DRAPE IN POSITION

[75] Inventor: Carl-Otto Hanssen, Kullavik, Sweden

[73] Assignee: Molnlycke AB, Gothenburg, Sweden

[21] Appl. No.: 800,434

[22] Filed: Nov. 21, 1985

[30] Foreign Application Priority Data

Dec. 11, 1984 [SE] Sweden .................. 8406283

[51] Int. Cl.⁴ .......................................... A61B 19/06
[52] U.S. Cl. ............................................... 128/132 D
[58] Field of Search .................................... 128/132 D

[56] References Cited

U.S. PATENT DOCUMENTS

| | | | |
|---|---|---|---|
| 3,667,458 | 6/1972 | Krebs | 128/132 D |
| 3,956,048 | 5/1976 | Nordgren | 128/132 D X |
| 4,196,723 | 4/1980 | Moose, Jr. | 128/132 D |
| 4,275,720 | 6/1981 | Wichman | 128/132 D |

*Primary Examiner*—Richard T. Stouffer
*Attorney, Agent, or Firm*—Young & Thompson

[57] ABSTRACT

The invention relates to an arrangement in a surgical drape. A prime characteristic feature of the arrangement is that it consists of a separate sheet assembly comprising an apertured attachment sheet, which is intended to be fastened over the area of a patient within which a surgical procedure is to be carried out, and a protective sheet which has a working aperture located therein and which is provided in a region around the aperture with structure for firmly fastening the protective sheet to the attachment sheet at the aforementioned region, such that the aperture in the attachment sheet lies opposite the working aperture in register therewith. This region of the protective sheet around the aperture is preferably rectangular in configuration and has the same shape and size as a working aperture in the surgical drape. Prior to putting the arrangement into use, the protective sheet is folded to a shape which fills an area congruent with the aforesaid region. Subsequent to positioning the surgical drape so that the working aperture thereof is in register with and surrounds the folding protective sheet, the sheet can be opened out through the working aperture and optionally fastened to the outwardly facing surface of the drape with the aid of fasteners. That side of the attachment sheet which is to face upwards when in use may be coated with a bonding agent externally of the region thereof joined to the protective sheet, thereby enabling a multi-part surgical drape to be fastened around the folded protective sheet.

4 Claims, 7 Drawing Figures

SURGICAL DRAPE AND ARRANGEMENT FOR SECURING THE SURGICAL DRAPE IN POSITION

The present invention relates to an arrangement in surgical drapes.

When using large surgical drapes of known kind, difficulties are often encountered in positioning and securing the drape in a manner such that the working aperture providing access to the area of the patient's body within which surgery is to be performed is in central alignment with said area. This is particularly true of large drapes intended for use when carrying out surgical procedures in and around the urethra, such as prostate surgery. The drapes used in such surgical procedures are namely provided with special leg portions, which cause the drape as a whole to be quite large and difficult to position correctly. The risk of infection when operating in the region of the urethra is also very high, and hence commensurately high conditions with respect to hygiene are required, necessitating inter alia, the drape to be arranged and fastened correctly with as few hand movements as possible.

In one known method of fastening surgical drapes of this kind, a smaller, apertured sheet is first positioned and secured around the area where surgery is to be performed, with the working aperture in the sheet located in register with said area. The smaller sheet is provided on the side thereof remote from the patient with a pressure-sensitive adhesive coating or like bonding agent covered with removable release paper. This paper must be removed prior to placing the drape in position, so as to expose the bonding agent or like pressure-sensitive adhesive, whereafter the drape is fastened to the sheet, with the working aperture in register with the aperture provided therein. This is difficult to achieve, however, owing to the fact that the drape is quite large and cumbersome, and is liable to fasten to the aforesaid exposed adhesive surface in the wrong position. Thus, the problem with this known method is that it requires a number of hand manipulations to be carried out, such as the removal of the aforesaid release paper, for example, with the subsequent serious risk of infection and with the risk of the drape being wrongly positioned. These problems are overcome, however, with an arrangement according to the present invention which is mainly characterized in that the arrangement consists of a separate sheet-assembly, comprising an apertured attachment sheet intended for attachment over the area within which surgical procedures are to be performed, referred to hereinafter as the surgical area, and a protective sheet which has a working aperture provided therein and which is provided within a region around said aperture with means for securely fastening the protective sheet to the attachment sheet at said region such that the apertures of respective sheets are in register with one another; in that said region is preferably of rectangular configuration and has the same shape and size as a working aperture provided in the surgical drape; in that prior to being used the protective sheet is folded to a shape which is congruent with the shape of the aforesaid region; and in that subsequent to positioning the surgical drape and its working aperture around the folded protective sheet said sheet can be opened out through the working aperture in said drape and optionally fastened to the outwardly facing surface thereof with the aid of fastening means intended herefor.

Such an apertured surgical drape can readily be arranged in the position desired without the use of adhesive fasteners or similar bonding agents, and will always be positioned correctly.

The invention will now be described in more detail with reference to the accompanying drawings, in which FIG. 1 is a side view of a double-folded surgical drape for use when performing surgery in the region of the urethra;

Figure 1:
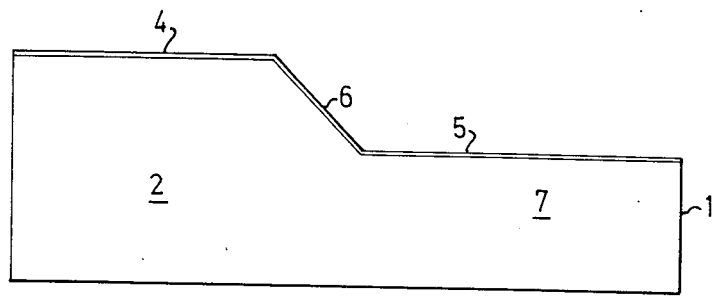

FIG. 1 illustrates a double-folded surgical drape for use when performing surgery in or around the urethra. The drape comprises a single elongated piece of material, referred to hereinafter as a surgical blank, which has been folded in two around its transverse centre line, to form a continuous end portion and an open end 1, whereafter the continuous end portion has been folded-in towards the open end 1, to form two leg portions 2,3, of which only the leg portion 2 is visible in FIG. 1. Subsequent to being folded in this way, the blank has been clipped or cut in the direction of its longitudinal axis, from the open end 1, parallel with its longitudinal axis, to the leg portions 2,3 formed when folding-in the aforesaid continuous end part, and then obliquely outwards towards the one edge 4 of respective leg portions of the drape blank. The straight and the obliquely cut edges are referenced 5 and 6 respectively in FIG. 1. The folded and clipped, or cut, drape blank has thereafter been joined along the cut edges 5 and also along the longitudinally extending edges 4 and the oblique edges 6 on respective leg portions. In this way there is formed firstly a rectangular drape-portion 7 which is intended to cover the torso of the patient and also to be draped over the anaesthetist's arch or trolley, and secondly the aforesaid leg portions 2,3 which are substantially in the form of a tent and which are intended to cover the legs of the patient and also the aforesaid surgical area. Before folding the drape blank, or subsequent thereto, there is formed therein a working aperture, which in the illustrated, prepared drape is located in the crutch region thereof between the leg portions 2,3. The working aperture is shown in FIG. 2, where it is referenced 8.

Figure 2:
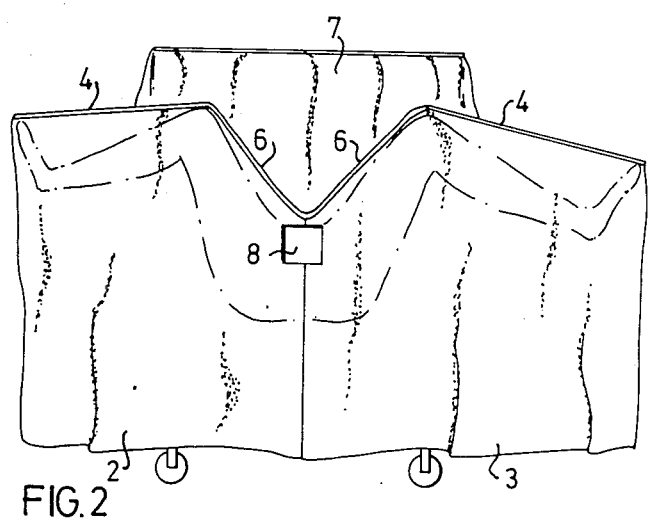
FIG. 2 illustrates the drape of FIG. 1 arranged over a patient.

FIG. 2 illustrates the use of the surgical drape described above with reference to FIG. 1. In FIG. 2 the legs of the patient have been drawn in chain lines and the figure as a whole is a perspective view seen in a direction towards the surgical area. As shown in FIG. 2, the geometry of the leg portions 2,3 is adapted to the attitude to which the patient's legs are placed when carrying out surgical procedures in or around the urethra. The oblique edges 6 of respective leg portions 2,3 rest against the upwardly facing surfaces of the patient's upper legs, whereas the connecting leg edges 4 extend from the patient's knees down to the feet of the patient. Consequently, as shown in FIG. 2, that part of the drape located around the working aperture 8, i.e. the sides of the leg portions 2,3 of the drape facing the theatre personnel, is perfectly smooth. As will also be seen from FIG. 2, the width of the leg portions 2,3 is suitably such that said leg portions reach down to the floor when the drape is in use.

Figure 3:
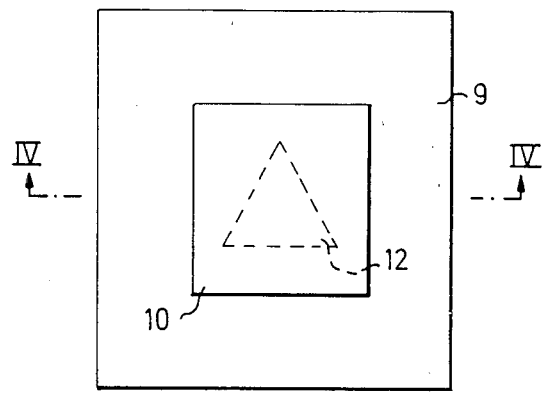
FIG. 3 is a view of an arrangement according to the invention, in the folded form in which it is positioned initially on the patient.
Figure 4:
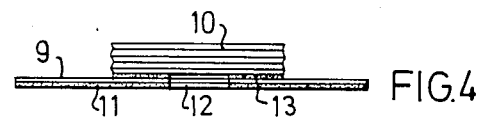
FIG. 4 is a sectional view of the arrangement according to FIG. 3, taken on the line IV—IV in said figure.

The FIG. 3 embodiment of an arrangement according to the invention for securing a surgical drape in position comprises an attachment sheet 9 which is intended to be bonded or similarly fastened to the patient's skin around the surgical area, and a protective sheet 10, which is shown in an initial folded state in FIGS. 3 and 4. The attachment sheet 9 is coated with a bonding agent 11 on the side thereof intended to lie against the patient's skin. Both the attachment sheet 9 and protective sheet 10 are perforated by a triangular working aperture 12. The attachment sheet 9 is fastened to the protective sheet 10 within a region thereof located around the working aperture of said sheet, by means of a pressure-sensitive coating or like bonded coating 13. The protective sheet 10 of the illustrated embodiment is folded into the shape of a square, when seen in a section extending parallel with the attachment sheet 9. This square area or region, is coated with a bonding agent, with the exception of that part thereof located centrally opposite the working aperture, as illustrated in FIG. 4. The working aperture 8 has a shape and size which coincides with the cross-sectional shape of the folded protective sheet.

Figure 5:
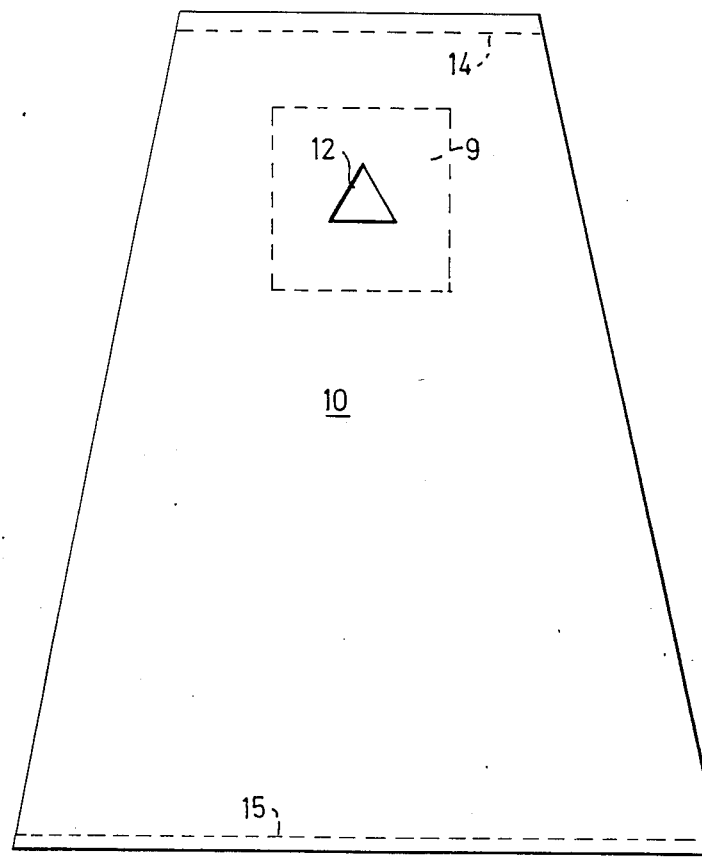
FIG. 5 illustrates the arrangement of FIGS. 3 and 4 when unfolded, said figure being drawn to a smaller scale.

When the attachment 9 of the drape-attachment sheet arrangement according to the invention has been arranged over the patient, all that is then required is for the working aperture 8 of the surgical drape to be brought into register with and around the commensurately folded protective sheet 10, which is then drawn through said aperture and unfolded. FIG. 5 illustrates the protective sheet 10 when unfolded. The ends of the protective sheet are provided with beads of bonding agent 14,15, for fastening the sheet to the outwardly facing surface of the surgical drape. The bead of bonding agent 15, or similar adhesive, on the lower end of the protective sheet may optionally be secured to a suitable part of the surgical coat or smock worn by the surgeon performing the operation.

Figure 6:
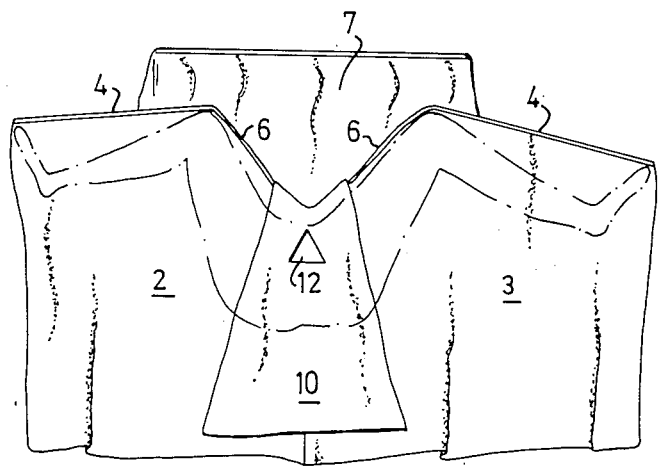
FIG. 6 illustrates how the surgical drape shown in FIGS. 1 and 2 is secured in place as desired, by means of the arrangement according to the invention illustrated in FIGS. 3-4.

FIG. 6 shows the protective sheet 10 when opened out through the working aperture 8 provided in the surgical drape illustrated in FIGS. 1 and 2. Since the shape and size of the working aperture 8 coincides with the adhesive-coated square region 13, the surgical drape is held firmly between the attachment sheet 9 and the protective sheet 10, against rotational forces.

Figure 7:
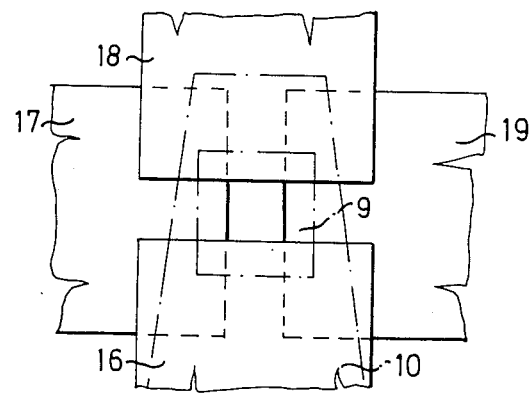
FIG. 7 illustrates how an arrangement according to the invention is used in combination with a surgical drape composed of four separate surgical sheets.

As illustrated by way of example in FIG. 7, an arrangement according to the invention can also be used in combination with a surgical drape comprising a plurality of separate surgical sheets. In FIG. 7 these separate surgical sheets are referenced 16,17,18 and 19, and the sheet-assembly comprising the attachment sheet 9 and the protective sheet 10 has been shown in chain lines. The attachment sheet 9 is placed over the surgical area with the protective sheet folded into the shape of a square, as described with reference to FIG. 3. The surgical sheets are then placed, one after the other, against a respective edge portion of the folded protective sheet, whereafter the protective sheet is opened out through the aperture thus defined by respective mutually adjacent edges of the surgical sheets forming the surgical drape. The separate surgical sheets are fastened to the upper side of the attachment sheet with the aid of a bonding agent, which may be provided on the surgical drape or on the upwardly facing surface of the attachment sheet.

Previously a surgical drape has comprised a plurality of surgical sheets, normally four in number. One serious disadvantage with such drapes, however, is that respective surgical sheets must be positioned and fastened by hand around the area where surgery is to be performed, this area being unprotected against contamination. When using the arrangement according to the invention, however, the surgical area is protected by the sheet assembly comprising the protective sheet and the attachment sheet. When textile sheets are used to form a large surgical drape, the protective sheet prevents those parts of the textile sheets bonded together with the aid of an adhesive or some other suitable fastening means from becoming wet, or excessively wet.

In addition to the advantages afforded by an arrangement according to the invention when positioning and fastening a surgical drape, the arrangement also affords the further advantage of enabling the protective sheet to be designed to fulfil particular functions. For example, the protective sheet may be provided with a liquid-collecting pocket or the like, not shown. This has obvious manufacturing advantages compared with drapes in which corresponding pockets or functions are incorporated in the actual surgical drape itself.

The invention is not limited to the aforesaid embodiments, since several modifications can be made within the scope of the claims.

It will be understood that the surgical drape may have any desired form, which also applies to the actual fastener arrangement. It is essential, however, that the folded protective sheet has external defining lines or boundary lines which delimit an angular surface area having the same shape and size as the working aperture in the surgical drape, and that the attachment sheet and the protective sheet are mutually connected within said area but externally of the working aperture passing through said sheets.

I claim:

1. In combination, a surgical drape with a working aperture and an arrangement for securing said surgical drape in position, said arrangement consisting of a separate sheet assembly comprising an attachment sheet with an aperture, said attachment sheet being adapted to be fastened over the area of a patient within which a surgical procedure is to be carried out, and a protective sheet which has a working aperture located therein and which is provided in a region around said protective sheet working aperture with means for firmly fastening the protective sheet to the attachment sheet at said region, such that the aperture in the attachment sheet lies opposite the working aperture in said protective sheet in register therewith; said region having a polygonal configuration and being of the same shape and size as said working aperture in the surgical drape; the protective sheet being adapted, prior to use, to be folded to a shape which fills an area congruent with the shape of said region; and the surgical drape being positioned on said attachment sheet with the working aperture of said surgical drape being of the same size and shape of and surrounding the protective sheet in said folded shape in register therewith, said protective sheet begin adapted to be opened out through the working aperture of said surgical drape subsequent to the positioning of said surgical drape on said attachment sheet.

2. An arrangement according to claim 1, characterized in that the side of the attachment sheet which is adapted to face away from the patient when in use is coated with a bonding agent externally of the region connected to the protective sheet, thereby enabling said surgical drape to be fastened to said attachment sheet around the folded protective sheet.

3. An arrangement according to claim 1, in which said surgical drape is a single surgical sheet.

4. An arrangement according to claim 1, in which said surgical drape is a plurality of surgical sheets having their edges defining said aperture of said surgical drape.

* * * * *